United States Patent [19]
Cox et al.

[11] Patent Number: 5,952,525
[45] Date of Patent: Sep. 14, 1999

[54] MANUFACTURE OF GLYPHOSATE SALTS

[75] Inventors: Brian Geoffrey Cox, Ponynton; Stephen Martin Brown, Upper Cumberworth; Thomas Gray, Midhurst, all of United Kingdom

[73] Assignee: ZENECA Limited

[21] Appl. No.: 09/068,381

[22] PCT Filed: Dec. 4, 1996

[86] PCT No.: PCT/GB96/02988

§ 371 Date: May 8, 1998

§ 102(e) Date: May 8, 1998

[87] PCT Pub. No.: WO97/22612

PCT Pub. Date: Jun. 26, 1997

[30]    Foreign Application Priority Data

Dec. 19, 1995 [GB] United Kingdom .................. 9525956

[51] Int. Cl.⁶ .................................. C07F 9/28; C07F 9/38
[52] U.S. Cl. ............................................... 562/69; 568/17
[58] Field of Search ................................... 568/69; 562/17

[56]    References Cited

U.S. PATENT DOCUMENTS

| | | |
|---|---|---|
| 4,315,765 | 2/1982 | Large . |
| 4,384,880 | 5/1983 | Large . |
| 4,431,594 | 2/1984 | Broadhurst et al. .............. 260/502.5 F |
| 4,437,874 | 3/1984 | Large . |
| 4,464,194 | 8/1984 | Prisbylla . |
| 5,300,680 | 4/1994 | Jones ......................................... 562/17 |
| 5,410,074 | 4/1995 | Jones ......................................... 562/17 |

FOREIGN PATENT DOCUMENTS

| | | |
|---|---|---|
| 0 369 076 A1 | 5/1990 | European Pat. Off. . |
| 08110638 | 10/1994 | Japan . |
| 92/21686 | 12/1992 | WIPO . |

OTHER PUBLICATIONS

CA:114:247527 abs of BR8806046, Jun. 1990.

*Primary Examiner*—Gary Geist
*Assistant Examiner*—Jean F Vollano
*Attorney, Agent, or Firm*—David P. LeCroy

[57]    ABSTRACT

The trimethylsulphonium salt of N-phosphonomethylglycine is prepared by reacting N-phosphonomethylglycine, preferably in the form of a solid, with an aqueous solution of trimethylsulphonium carbonate or trimethylsulphonium bicarbonate or a mixture thereof. The trimethylsulphonium carbonate or trimethylsulphonium bicarbonate may be prepared by bubbling carbon dioxide through an aqueous solution of trimethylsulphonium hydroxide. It is possible to manufacture trimethylsulphonium carbonate or bicarbonate at one site and then transport them to a different site for local manufacture of N-phosphonomethylglycine in a relatively unsophisticated plant which produces minimal effluent.

10 Claims, No Drawings

MANUFACTURE OF GLYPHOSATE SALTS

This application is the national stage of PCT/GB96/02988 filed Dec. 4, 1996.

This invention relates to the manufacture of glyphosate salts, and in particular to the manufacture of the trimethylsulfonium salt of glyphosate, to the manufacture of trimethylsulfonium intermediates and to novel trimethylsulfonium intermediates.

U.S. Pat. No. 4,431,594 describes a process for the preparation of organic salts of N-phosphonomethylglycine which comprises reacting N-phosphonomethylglycine with a compound of formula R1R2R3S+=ZX−(a) wherein R1, R2 and R3 are the same or different and are alkyl groups having from 1 to 4 carbon atoms or aromatic alkyl groups, X is chloride, bromide or iodide and Z is an electron pair or oxygen, in the presence of a trialkylarmine and isolating the product by phase separation between water and a polar functional solvent which is immiscible with water. Preferred compounds of formula (a) include trimethylsulfonium chloride and preferred trialkylamines include ALAMINE 336 (ALAMINE is a trade mark of Henkel Co.). Whilst this process is very effective for use on a major manufacturing site having plant capable of handling the relatively complex stages required for the recycle and regeneration of the amine, there is a need for a process in which the trimethylsulfonium salt of N-phosphonomethylglycine is manufactured from the parent acid N-phosphonomethylglycine using relatively unsophisticated plant.

In European Patent Application No 0639198 there is described a process for the preparation of a salt such as a trimethylsulfonium salt of N-phosphonomethylglycine in which the parent acid N-phosphonomethylglycine is reacted with trimethylsulfonium hydrogen sulfate in the presence of a base. In a preferred embodiment, ammonium hydroxide is used as base to form a product which contains both the trimethylsulfonium salt of N-phosphonomethylglycine and ammonium sulfate. Whilst this process is highly efficient for the manufacture of formulations in which ammonium sulfate is a required additive, ammonium sulfate is not necessarily a desired component of all formulations of the the trimethylsulfonium salt of N-phosphonomethylglycine.

We have now found that the use of trimethylsulfonium carbonate or trimethylsulfonium bicarbonate as starting material for the manufacture of the trimethylsulfonium salt of N-phosphonomethylglycine provides a process which produces the desired product in excellent yield and at high concentration and which is capable of being operated under ambient conditions in relatively unsophisticated plant and with minimal effluent control requirements.

According to the present invention there is provided a process for the manufacture of the trimethylsulfonium salt of N-phosphonomethylglycine which comprises reacting N-phosphonomethylglycine with an aqueous solution of trimethylsulfonium carbonate or trimethylsulfonium bicarbonate or a mixture thereof.

The reaction of N-phosphonomethylglycine with trimethylsulfonium carbonate requires two moles of N-phosphonomethylglycine per mole of trimethylsulfonium carbonate and produces two moles of the trimethylsulfonium salt of N-phosphonomethylglycine. Substantially stoichiometric proportions are conveniently used. A slight excess of either component, for example up to 5% excess of trimethylsulfonium carbonate per mole of N-phosphonomethylglycine may be used if desired.

The reaction of N-phosphonomethylglycine with trimethylsulfonium bicarbonate requires one mole of N-phosphonomethylglycine per mole of trimethylsulfonium bicarbonate and produces one mole of the trimethylsulfonium salt of N-phosphonomethylglycine. Substantially stoichiometric proportions are conveniently used. A slight excess of either component, for example up to 5% excess may be used if desired.

Whether trimethylsulfonium carbonate or bicarbonate or a mixture thereof is used as starting material, the only product other than the trimethylsulfonium salt of N-phosphonomethylglycine is carbon dioxide which is readily vented to atmosphere and requires no sophisticated effluent control procedures.

An aqueous solution of N-phosphonomethylglycine may be used if desired as starting material, but it is preferred to add solid N-phosphonomethylglycine to an aqueous solution of the trimethylsulfonium carbonate or bicarbonate. It is an advantage of this embodiment of the process of the present invention that relatively concentrated aqueous solutions of the trimethylsulfonium salt of N-phosphonomethylglycine can be prepared and can be used for high-strength commercial formulations without the need to remove water. We have found for example that solutions as concentrated as 720 g/l or more of the trimethylsulfonium salt of N-phosphonomethylglycine in water may be prepared using the process of the present invention.

The solid N-phosphonomethylglycine is preferably added over a period of time sufficient to avoid excessive frothing resulting from the generation of carbon dioxide.

Trimethylsulfonium carbonate and bicarbonate are believed to be novel compounds. Thus according to a further aspect of the present invention there is provided trinethylsulfonium carbonate and trimethylsulfonium bicarbonate.

We have found that trimethylsulfonium carbonate and bicarbonate are relatively stable compounds. In particular it is possible to manufacture trimethylsulfonium carbonate or bicarbonate on one site and then transport it to a second site where the reaction with N-phosphonomethylglycine takes place in a very simple plant in which the reaction takes place in a single reactor with a requirement for only minimal effluent control. Trimethylsulfonium bicarbonate has an essentially neutral pH and is storage-stable for extended periods of time. Thus trimethylsulfonium bicarbonate is preferred when manufacture of the trimethylsulfonium salt takes place on one site and is then transported to a distant second site where the reaction with N-phosphonomethylglycine takes place.

Trimethylsulfonium carbonate and bicarbonate may conveniently be prepared by bubbling carbon dioxide through an aqueous solution of trimethylsulfonium hydroxide until the appropriate pH is reached (pH 7.3 for the bicarbonate and pH 11.4 for the carbonate). If the reaction is halted at an intermediate stage, a mixture of the bicarbonate and carbonate will be formed.

Trimethylsulphonium hydroxide is a known compound which may be prepared by a variety of ways known in the art. Trimethylsulfonium hydroxide is stable in aqueous solution under normal operating conditions but is insufficiently stable to permit long-term storage such as would be required for example if trimethylsulfonium hydroxide were to be manufactured at one site and then transported to another site for conversion to the trimethylsulfonium salt of N-phosphonomethylglycine. It is preferred therefore that the trimethylsulfonium carbonate or bicarbonate is prepared by an integrated process in which trimethylsulfonium hydroxide is present only as an intermediate having a relatively short storage life. It is not necessary to isolate the trimethylsulfonium hydroxide intermediate.

Trimethylsulfonium carbonate or bicarbonate for use in the process of the present invention may be prepared by (i) reacting an aqueous solution of trimethylsulfonium hydrogen sulfate with barium hydroxide to form trimethylsulfonium hydroxide and an insoluble barium salt, (ii) filtering to remove the insoluble barium salt and (ii) reacting the resultant solution with gaseous carbon dioxide until the pH of the solution reaches about pH 11.4 if trimethylsulfonium carbonate is the desired product and about pH 7.3 if the bicarbonate is the desired product.

Trimethylsulfonium hydrogen sulfate may be prepared as described in European Patent Application No 0639198.

In an alternative process, trimethylsulfonium bicarbonate may be prepared by the reaction of trimethylsulfonium iodide, hydrogen peroxide and carbon dioxide. An aqueous solution of trimethylsulfonium iodide is convenient saturated with carbon dioxide and hydrogen peroxide solution is then added slowly whilst maintaining a carbon dioxide sparge. The conversion of the trimethylsulfonium iodide to the hydroxide is conveniently monitored by means of the pH of the reaction mixture, the reaction being complete when the pH reaches about pH 7.6. Iodine formed during the reaction may conveniently be recovered by solvent extraction. Substantially stoichiometric quantities of the reactants are suitably used, although there may be advantages in the use of a slight excess of hydrogen peroxide relative to the trimethylsulfonium iodide. The reaction conveniently takes place under ambient conditions.

Free Iodine produced during the above reaction is preferably recovered and converted back to trimethylsulfonium iodide for re-cycle. A variety of re-cycle processes are possible and will occur to those skilled in the art. Thus for example the iodine recovered from the product may be converted to methyl iodide which is then reacted with dimethylsulfide according to well-known procedures. A number of processes are available for the conversion of free iodine to methyl iodide. Thus for example the free iodine may be converted to phosphorous tri-iodide by reaction with phosphorous and the product converted by reaction with methanol to methyl iodide. Typically the phosphorous and methanol are pre-mixed and heated to reflux. The condensate from the reflux is passed through a small, secondary reactor which contains the iodine, and the resulting iodine in methanol solution is allowed to return to the main reaction to provide a controlled addition of iodine to the system. If a water-immiscible immiscible solvent is used to extract free iodine from the reaction, the solvent is preferably selected to integrate with this process.

In a preferred integrated process for the manufacture of trimethylsulfonium carbonate or bicarbonate for use in the process of the present invention, trimethylsulfonium hydrogen sulfate is treated with an alkali such as sodium hydroxide to precipitate sodium sulfate which is removed by filtration, leaving a solution of trimethylsulfonium hydroxide through which carbon dioxide is bubbled to prepare the trimethylsulfonium carbonate or bicarbonate or a mixture thereof as previously described. The reaction conveniently takes place in a single reactor and the carbon dioxide may be added either before or after the filtration to remove the sodium sulfate. The reaction preferably takes place in concentrated solution to minimise the quantity of sodium ion remaining in solution. Thus for example the quantity of trimethylsulfonium hydrogen sulfate present in the starting solution is preferably from about 50% by weight to about 85% by weight. Substantially stoichiometric proportions of sodium hydroxide are preferably used.

If the trimethylsulfonium hydrogen sulfate is prepared for example as described in EP 0639198 by reaction of dimethylsulfide, methanol and sulfuric acid, the reaction product will normally contain excess sulfuric acid and methylhydrogen sulfate formed by the reaction of methanol and sulfuric acid. Sufficient sodium hydroxide should be added to Is neutralise these species and precipitate sodium sulfate. The quantity of sodium hydroxide required may be calculated from the proportions of the reactants used to manufacture the trimethylsulfonium hydrogen sulfate, the requirements being two moles of sodium hydroxide per mole of free sulfuric acid, one mole of sodium hydroxide per mole of methylhydrogen sulfate and about 2 moles of sodium hydroxide per mole of trimethylsulfonium hydrogen sulfate. In practice, the reaction product containing trimethylsulfonium hydrogen sulfate is conveniently neutralised to pH 7 using sodium hydroxide and thereafter a further mole of sodium hydroxide per mole of trimethylsulfonium hydrogen sulfate is added.

The reaction conveniently takes place substantially at ambient temperature although since the reaction is exothermic, cooling may be provided if required.

As noted above, the trimethylsulfonium carbonate and especially the trimethylsulfonium bicarbonate are suitable for transportation to a site for local manufacture of the trimethylsulfonium salt of glyphosate. We have found that trimethylsulfonium bicarbonate is highly soluble in water and it is feasible therefore to transport a concentrated solution of the product rather than undertake the cost of isolating a solid. If desired, the aqueous solution trimethylsulfonium carbonate or bicarbonate prepared by the reaction of carbon dioxide and trimethylsulfonium hydroxide may be concentrated prior to transportation, for example by distillation under reduced pressure.

Thus according to a further aspect of the present invention there is provided a process for the manufacture of the trimethylsulfonium salt of N-phosphonomethylglycine which comprises (i) bubbling carbon dioxide through an aqueous solution of trimethylsulfonium hydroxide to form trimethylsulfonium bicarbonate or trimethylsulfonium carbonate or a mixture thereof, (ii) optionally obtaining the trimethylsulfonium bicarbonate or carbonate or the mixture thereof as a transportable solid or a concentrated aqueous solution, and (iii) reacting N-phosphonomethylglycine with an aqueous solution of trimethylsulfonium bicarbonate or carbonate or the mixture thereof.

According to a still further aspect of the present invention there is provided a process for the manufacture of the trimethylsulfonium salt of N-phosphonomethylglycine which comprises (i) treating trimethylsulfonium hydrogen sulfate with sodium hydroxide to precipitate sodium sulfate (ii) bubbling carbon dioxide through the resultant aqueous solution of trimethylsulfonium hydroxide to form trimethylsulfonium bicarbonate or carbonate or a mixture thereof, (iii) removing the precipitated sodium sulfate either after stage (i) or stage (ii), (iv) optionally obtaining the trimethylsulfonium bicarbonate or carbonate or the mixture thereof as a transportable solid or concentrated aqueous solution, and (v) reacting N-phosphonomethylglycine with an aqueous solution of trimethylsulfonium bicarbonate or carbonate.

According to a still further aspect of the present invention there is provided a process for the manufacture of the trimethylsulfonium salt of N-phosphonomethylglycine which comprises (i) reacting an aqueous solution of trimethylsulfonium hydrogen sulfate with barium hydroxide to form trimethylsulfonium hydroxide and an insoluble barium salt, (ii) filtering to remove the insoluble barium salt (iii) reacting the resultant solution with gaseous carbon dioxide to form trimethylsulfonium carbonate or bicarbonate or a mixture thereof (iv) optionally obtaining the trimethylsulfonium bicarbonate or carbonate or the mixture thereof as a transportable solid or a concentrated aqueous solution, and (v) reacting N-phosphonomethylglycine with an aqueous solution of trimethylsulfonium bicarbonate or carbonate or the mixture thereof.

According to a still further aspect of the present invention there is provided a process for the manufacture of the trimethylsulfonium salt of N-phosphonomethylglycine which comprises (i) reacting trimethylsulfonium iodide, hydrogen peroxide and carbon dioxide to form trimethylsulfonium hydroxide and free iodine (ii) reacting the resultant solution with gaseous carbon dioxide to form trimethylsulfonium carbonate or bicarbonate or a mixture thereof (iii) optionally obtaining the trimethylsulfonium bicarbonate or carbonate or the mixture thereof as a transportable solid or a concentrated aqueous solution, and (v) reacting N-phosphonomethylglycine with an aqueous solution of trimethylsulfonium bicarbonate or carbonate or the mixture thereof.

The invention is illustrated by the following Examples in which all parts and percentages are by weight unless otherwise stated.

EXAMPLE 1

This Example illustrates the preparation of the trimethylsulfonium salt of N-phosphonomethylglycine by reaction of trimethylsulfonium bicarbonate and N-phosphonomethylglycine.

To 50.8 g of a solution (77.7%) of trimethylsulfonium bicarbonate in water was further water to give a 46.4% trimethylsulfonium bicarbonate solution at pH 7.3 which was charged to a vessel fitted with a stirrer and charging funnel. The solution was stirred at room temperature and 52.1 g of solid N-phosphonomethylglycine acid (91.0% strength) was added in aliquots. Frothing due to the release of carbon dioxide was allowed to subside between additions. A clear solution of the trimethylsulfonium salt of N-phosphonomethylglycine was obtained in substantially quantitative yield as determined by HPLC analysis of N-phosphonomethylglycine.

EXAMPLE 2

This Example illustrates the preparation of the trimethylsulfonium salt of N-phosphonomethylglycine by reaction of trimethylsulfonium carbonate and N-phosphonomethylglycine.

To 77.2 g of a solution (45.1%) of trimethylsulfonium carbonate in water was added a further 7.8 g of water in a vessel fitted with a stirrer and charging funnel. The solution was stirred at room temperature and 57.3 g of solid N-phosphonomethylglycine acid (94.1% strength) was added in aliquots. Frothing due to the release of carbon dioxide was allowed to subside between additions. A clear solution of the trimethylsulfonium salt of N-phosphonomethylglycine was obtained in substantially quantitative yield as determined by HPLC analysis of N-phosphonomethylglycine.

EXAMPLE 3

This Example illustrates the preparation of trimethylsulfonium carbonate from trimethylsulfonium hydroxide.

A solution of trimethylsulfonium carbonate (27.1 g of solution of 7.34% strength) was charged to a stirred vessel. The pH at this stage was 13. Carbon dioxide was bubbled through the solution using a sinter until the pH dropped to 11.4. Trimethylsulfonium carbonate was obtained in substantially stoichiometric yield as measured by ion chromatography determination of trimethylsulfonium ion.

EXAMPLE 4

This Example illustrates the preparation of trimethylsulfonium bicarbonate from trimethylsulfonium iodide. Solid trimethylsulfonium iodide (51.3 g at 98.9% strength) was diluted with 200 ml water and charged to a jacketed reaction vessel fitted with a 4-blade turbine agitator, condenser, thermometer, gas sparging tube and pH probe. The initial pH of the solution was 4.9.

Carbon dioxide was bubbled through the solution using a sinter for 30 minutes to ensure saturation and then hydrogen peroxide solution (7.0 g of 60.0% strength) diluted with 100 ml water was added using a syringe pump at a rate of 18 ml per hour whilst maintaining the carbon dioxide sparge. The pH of the solution was monitored throughout the addition and reached a final pH of 7.6. Iodine was then removed from the reaction mixture using successive washings with dichloromethane. A yield of 73% of trimethylsulfonium bicarbonate was obtained as measured by ion chromatography analysis of the trimethylsulfonium ion.

EXAMPLE 5

This Example illustrates the preparation of trimethylsulfonium bicarbonate from trimethylsulfonium hydrogen sulfate.

A solution of trimethylsulfonium hydrogen sulfate (50.2 g of a solution at 68% strength) and an additional 50 ml water were charged to a reaction vessel fitted with stirrer, thermometer, condenser and charging funnel. Barium hydroxide (57.8 g) was added in aliquots whilst maintaining the temperature at 20°–25° C. The resulting slurry was stirred for a further 3 hours after which a further 50 ml of water was added and the slurry was filtered under vacuum.

Testing of the filtrates showed the presence of sulfate (barium chloride test) and a further portion of barium hydroxide (4.6 g) was added to the filtrates and the mixture was stirred for one hour. The slurry was again filtered under vacuum and on this occasion no sulphate ion was detected in the filtrates.

The resulting solution of trimethylsulfonium hydroxide was charged to a reaction vessel and carbon dioxide was bubbled through the solution using a sinter until the pH of the solution dropped to 7.3. A yield of 90.8% of trimethylsulfonium bicarbonate was obtained as measured by ion chromatography determination of trimethylsulfonium ion.

EXAMPLES 6

Trimethylsulfonium hydrogen sulfate (59.8 g at 75% strength by weight) was placed in a four-neck round bottomed flask and sodium hydroxide solution (57.0 g at 47% strength by weight) was added slowly with agitation whilst maintaining the temperature below 30° C. with cooling. The precipitated sodium hydrogen sulfate was filtered off and the filter cake washed with 12 g of iced water. The filtrates and wash were combined and carbon dioxide was bubbled through until the pH of the solution was 8.5 (indicating the presence of some carbonate in addition to the bicarbonate). More sodium sulfate was precipitated, filtered off and washed with 10 g of iced water. The filtrate (72 g) was analysed and found to contain $1.13 \times 10^{-3}$ gmoles sulfate ion, 0.1886 gmoles bicarbonate ion, 0.015 gmoles sodium ion and 0.015 gmoles carbonate ion. The yield based on trimethylsulfonium hydrogen sulfate was 90%.

We claim:

1. A process for the manufacture of the trimethylsulfonium salt of N-phosphonomethylglycine which comprises reacting N-phosphonomethylglycine with an aqueous solution of trimethylsulfonium carbonate or trimethylsulfonium bicarbonate or a mixture thereof.

2. A process as claimed in claim 1 wherein there is used substantially stoichiometric proportions of trimethylsulfonium carbonate or trimethylsulfonium bicarbonate respectively.

3. A process as claimed in claim 1 wherein solid N-phosphonomethylglycine is added to an aqueous solution of trimethylsulfonium carbonate or trimethylsulfonium bicarbonate.

4. A process for the manufacture of the trimethylsulfonium salt of N-phosphonomethylglycine which comprises (i) bubbling carbon dioxide through an aqueous solution of trimethylsulfonium hydroxide to form trimethylsulfonium bicarbonate or trimethylsulfonium carbonate or a mixture thereof, (ii) optionally obtaining the trimethylsulfonium bicarbonate or carbonate or the mixture thereof as a transportable solid or a concentrated aqueous solution, and (iii) reacting N-phosphonomethylglycine with an aqueous solution of trimethylsulfonium bicarbonate or carbonate or the mixture thereof.

5. A process for the manufacture of the trimethylsulfonium salt of N-phosphonomethylglycine which comprises (i) treating trimethylsulfonium hydrogen sulfate with sodium hydroxide to precipitate sodium sulfate (ii) bubbling carbon dioxide through the resultant aqueous solution of trimethylsulfonium hydroxide to form trimethylsulfonium bicarbonate or carbonate or a mixture thereof, (iii) removing the precipitated sodium sulfate either after stage (i) or stage (ii), (iv) optionally obtaining the trimethylsulfonium bicarbonate or carbonate or the mixture thereof as a transportable solid or concentrated aqueous solution, and (v) reacting N-phosphonomethylglycine with an aqueous solution of trimethylsulfonium bicarbonate or carbonate.

6. A process for the manufacture of the trimethylsulfonium salt of N-phosphonomethylglycine which comprises (i) reacting an aqueous solution of trimethylsulfonium hydrogen sulfate with barium hydroxide to form trimethylsulfonium hydroxide and an insoluble barium salt, (ii) filtering to remove the insoluble barium salt (iii) reacting the resultant solution with gaseous carbon dioxide to form trimethylsulfonium carbonate or bicarbonate or a mixture thereof (iv) optionally obtaining the trimethylsulfonium bicarbonate or carbonate or the mixture thereof as a transportable solid or a concentrated aqueous solution, and (v) reacting N-phosphonomethylglycine with an aqueous solution of trimethylsulfonium bicarbonate or carbonate or the mixture thereof.

7. A process for the manufacture of the trimethylsulfonium salt of N-phosphonomethylglycine which comprises (i) reacting trimethylsulfonium iodide, hydrogen peroxide and carbon dioxide to form trimethylsulfonium hydroxide and free iodine (ii) reacting the resultant solution with gaseous carbon dioxide to form trimethylsulfonium carbonate or bicarbonate or a mixture thereof (iii) optionally obtaining the trimethylsulfonium bicarbonate or carbonate or the mixture thereof as a transportable solid or a concentrated aqueous solution, and (v) reacting N-phosphonomethylglycine with an aqueous solution of trimethylsulfonium bicarbonate or carbonate or the mixture thereof.

8. A process according to claim 7 wherein the free iodine is recovered and re-cycled.

9. Trimethylsulfonium bicarbonate.

10. Trimethylsulfonium carbonate.

* * * * *